United States Patent [19]

White et al.

[11] 4,219,480

[45] Aug. 26, 1980

[54] PROCESS FOR THE PRODUCTION OF 2-ARYL-2H-BENZOTRIAZOLES

[75] Inventors: Howard L. White, Warwick; Casimir V. Krolewski, Coventry, both of R.I.

[73] Assignee: Ciba-Geigy Corporation, Ardsley, N.Y.

[21] Appl. No.: 835,074

[22] Filed: Sep. 20, 1977

Related U.S. Application Data

[63] Continuation of Ser. No. 668,343, Mar. 19, 1976, abandoned, which is a continuation-in-part of Ser. No. 577,386, May 14, 1975, abandoned.

[51] Int. Cl.$^2$ .............................................. C07D 249/20
[52] U.S. Cl. ...................................... 548/260; 548/259
[58] Field of Search ..................... 260/308 B; 548/259, 548/260

[56] References Cited

U.S. PATENT DOCUMENTS

| 3,978,074 | 8/1976 | Jancis | 260/308 B |
| 4,041,044 | 8/1977 | White | 260/308 B |

FOREIGN PATENT DOCUMENTS 48-26012  8/1973  Japan .................................. 260/308 B

*Primary Examiner*—Paul M. Couglan, Jr.
*Attorney, Agent, or Firm*—Luther A. R. Hall

[57] ABSTRACT

A process for the production of 2-aryl-2H-benzotriazoles comprises reducing and cyclizing the corresponding o-nitroazobenzenes with hydrogen at a temperature in the range of about 20° C. to about 100° C. and at a pressure in the range of about 15 psia (1 atmosphere) to about 1000 psia (66 atmospheres) in an alkaline medium at a pH over 10 in the presence of a nickel catalyst, preferably molybdenum-promoted Raney nickel. High yields of pure product are obtained directly with a concomitant reduction of undesired by-product and a reduction in effluent pollution problems.

23 Claims, No Drawings

PROCESS FOR THE PRODUCTION OF 2-ARYL-2H-BENZOTRIAZOLES

This application is a continuation of application Ser. No. 668,343, filed on Mar. 19, 1975, now abandoned, which in turn is a continuation-in-part of application Ser. No. 577,386, filed May 14, 1975, now abandoned.

BACKGROUND OF THE INVENTION

This invention pertains to a process for the preparation of 2-aryl-2H-benzotriazoles and derivatives thereof. More particularly, the invention relates to a novel process for preparing 2-aryl-2H-benzotriazoles whereby high yields of the desired products are obtained and effluent pollution problems occurring with present processes for making such products are essentially eliminated.

Heretofore, the conversion of an ortho-nitroazobenzene to the corresponding 2-aryl-2H-benzotriazole has been accomplished by chemical and electrolytic reduction processes. For example, as seen in U.S. Pat. Nos. 3,072,585 and 3,230,194, o-nitroazobenzene derivatives have been chemically reduced utilizing zinc in alcoholic sodium hydroxide solutions to give good yields of the corresponding 2-aryl-2H-benzotriazoles. Ammonium sulfide, alkali sulfides, zinc with ammonia at 80°–100° C., sodium hydrosulfide and zinc with hydrochloric acid have also been used as the chemical reducing agents for this transformation as disclosed in U.S. Pat. No. 2,362,988. The use of ammonium sulfide was also reported by S. N. Chakrabarty et al, *J. Indian Chem. Soc.*, 5, 555 (1928); *Chem. Abst.*, 23, 836, (1929) with mixed results depending on the presence or absence of substituent groups on the 2-aryl group. In some cases the desired 2-aryl-2H-benzotriazoles were not formed at all with the products of reduction being only the corresponding o-aminoazobenzenes.

Electrolytic reduction of o-nitroazobenzenes was reported by H. Itomi, *Mem. Coll. Sci. Kyoto Imp. Univ.*, 12A, No. 6, 343 (1929); *Chem. Abst.*, 24, 2060 (1930) with the use of a copper cathode in dilute sodium hydroxide solution. Yields varied from 25 to 60% depending on specific embodiments and conditions with a major impurity being formed, namely the corresponding o-aminoazobenzene.

The widely used zinc dust and sodium hydroxide chemical reducing system for transforming o-nitroazobenzenes into the corresponding 2-aryl-2H-benzotriazoles was reported by K. Elbs, et al, *J. Prakt. Chem.*, 108, 204 (1924); *Chem. Abst.*, 19, 514 (1925). The yields of the desired 2-aryl-2H-benzotriazoles varied from 30 to 85% depending on the specific o-nitroazobenzene intermediate reduced.

The known chemical and electrolytic reduction processes for preparing 2-aryl-2H-benzotriazoles are not practical or economically attractive in many cases. The widely used zinc dust and sodium hydroxide system produces effluent pollution problems in respect to waste disposal of zinc sludge which is of increasing environmental concern.

The preparation in good yield of the isomeric, but chemically distinct 1H-benzotriazoles by the catalytic reduction in alkaline medium of o-nitrophenylhydrazine and selected phenyl ring substituted alkyl and perfluoroalkyl derivatives thereof was reported in Japanese patent publication, Sho 48-26012, Aug. 3, 1973. The isomeric 2H-benzotriazoles of this invention cannot be prepared from phenylhydrazines.

It is therefore an object of this invention to provide a novel process for the preparation of 2-aryl-2H-benzotriazoles avoiding severe pollution and environmental problems.

A further object of this invention is to prepare 2-aryl-2H-benzotriazoles by reducing and cyclizing the corresponding o-nitroazobenzene under certain conditions hereinafter set forth in greater detail whereby high yields of the products can be obtained in acceptable purity.

DETAILED DISCLOSURE

Taken in its broadest aspect, one embodiment of this invention is found in a process for the production of 2-(2-hydroxy-5-methylphenyl)-2H-benzotriazole which comprises reducing and cyclizing 2-nitro-2'-hydroxy-5'-methylazobenzene with hydrogen at reducing conditions in an aqueous alkaline medium in the presence of a nickel hydrogenation catalyst, and recovering the desired 2-(2-hydroxy-5-methyl)-2H-benzotriazole.

Taken in its broadest aspect, another embodiment of this invention is found in a process for the production of 2-(2-hydroxy-5-methylphenyl)-2H-benzotriazole which comprises reducing and cyclizing 2-nitro-2'-hydroxy-5'-methylazobenzene with hydrogen at reducing conditions in an alkaline aqueous organic medium in the presence of a nickel hydrogenation catalyst, and recovering the desired 2-(2-hydroxy-5-methyl)-2H-benzotriazole.

Taken in its broadest aspect, still another embodiment of this invention is found in a process for the production of 2-(2-hydroxy-3,5-di-tert-amylphenyl)-2H-benzotriazole which comprises reducing and cyclizing 2-nitro-2'-hydroxy-3',5'-di-tert-amylazobenzene with hydrogen at reducing conditions in an organic solvent system containing a water-soluble amine in the presence of a nickel hydrogenation catalyst and recovering the desired 2-(2-hydroxy-3,5-di-tert-amylphenyl)-2H-benzotriazole.

The process of this invention can be carried out at a temperature in the range of from about 20° C. to about 100° C., preferably from about 30° C. to about 80° C., and most preferably from about 40° C. to about 70° C.

A further embodiment of this invention is found in a process for the production of 2-(2-hydroxy-5-methylphenyl)-2H-benzotriazole which comprises treating 2-nitro-2'-hydroxy-5'-methylazobenzene with hydrogen at a temperature in the range of from about 20° C. to about 100° and at a pressure in the range of about 15 psia (1.05 kg/cm$^2$, 1 atmosphere) to about 1000 pounds per square inch (about 70 kg/cm$^2$, 66 atmospheres) in an aqueous alkaline medium in the presence of promoted or unpromoted nickel hydrogenation catalyst, removing the nickel catalyst by filtration, lowering pH of the aqueous system to a value less than 10 to precipitate the desired product, and recovering the desired 2-(2-hydroxy-5-methylphenyl)-2H-benzotriazole by conventional procedures. The preferred alkaline medium is an aqueous alkali metal hydroxide solution.

A further embodiment of this invention is found in a process for the production of 2-(2-hydroxy-5-methylphenyl)-2H-benzotriazole which comprises treating 2-nitro-2'-hydroxy-5'-methylazobenzene with hydrogen at a temperature in the range of from about 20° C. to about 100° C. and at a pressure in the range of about 15 psia (1.05 kg/cm$^2$, 1 atmosphere) to about 1000 pounds per square inch (about 70 kg/cm$^2$, 66 atmospheres) in an alkaline aqueous organic (preferably isopropanol) medium in the presence of a promoted or unpromoted nickel hydrogenation catalyst, removing the catalyst by filtration, lowering the pH of the aqueous system to a value less than 4 to precipitate the desired product, and recovering the desired 2-(2-hydroxy-5-methylphenyl)-2H-benzotriazole by conventional procedures. The preferred alkaline medium is an aqueous alkali metal hydroxide/alkanol solution.

A further embodiment of this invention is found in a process for the production of 2-(2-hydroxy-3,5-di-tert-amylphenyl)-2H-benzotriazole which comprises treating 2-nitro-2'-hydroxy-3',5'-di-tert-amylazobenzene with hydrogen at a temperature in the range of from about 20° C. to about 100° C. and at a pressure in the range of about 15 psia (1.05 kg/cm$^2$, 1 atmosphere) to about 1000 pounds per square inch (about 70 kg/cm$^2$, 66 atmospheres) in an organic solvent system containing a water-soluble amine, preferably isopropanol/diethylamine, in the presence of a promoted or unpromoted nickel hydrogenation catalyst, removing the metal catalyst by filtration, and recovering the desired 2-(2-hydroxy-3,5-di-tert-amylphenyl)-2H-benzotriazole by conventional procedures.

A further embodiment of this invention is found in a process for the production of 2-(2-hydroxy-5-methylphenyl)-2H-benzotriazole which comprises treating 2-nitro-2'-hydroxy-5'-methylazobenzene with hydrogen at a temperature in the range of from about 20° C. to about 100° C. and at a pressure in the range of about 15 psia (1.05 kg/cm$^2$, 1 atmosphere) to about 1000 pounds per square inch (about 70 kg/cm$^2$, 66 atmospheres) in an organic solvent system containing a water-soluble amine (preferably toluene/methanol/diethylamine) in the presence of a promoted or unpromoted nickel hydrogenation catalyst, removing the metal catalyst by filtration, and recovering the desired 2-(2-hydroxy-5-methylphenyl)-2H-benzotriazole by conventional procedures.

A specific embodiment of the invention is exemplified in a process for the production of 2-(2-hydroxy-5-methylphenyl)-2H-benzotriazole, which comprises treating 2-nitro-2'-hydroxy-5'-methylazobenzene with hydrogen at a temperature in the range of from about 20° C. to about 100° C. and at a pressure in the range of a from about 15 psia to about 1000 pounds per square inch (about 1.05 to about 70 kg/cm$^2$) in an aqueous alkaline medium in the presence of a hydrogenation catalyst comprising molybdenum-promoted Raney nickel, and recovering the desired 2-(2-hydroxy-5-methylphenyl)-2H-benzotriazole.

A specific embodiment of the invention is exemplified in a process for the production of 2-(2-hydroxy-5-methylphenyl)-2H-benzotriazole, which comprises treating 2-nitro-2'-hydroxy-5'-methylazobenzene with hydrogen at a temperature in the range of from about 20° C. to about 100° C. and at a pressure in the range of from about 15 psia to about 1000 pounds per square inch (about 1.05 to about 70 kg/cm$^2$) in an alkaline aqueous organic medium, preferably aqueous sodium hydroxide/isopropanol, in the presence of a hydrogenation catalyst comprising molybdenum-promoted Raney nickel, and recovering the desired 2-(2-hydroxy-5-methylphenyl)-2H-benzotriazole.

Another specific embodiment of the invention is exemplified in a process for the production of 2-(2-hydroxy-3,5-di-tert-amylphenyl)-2H-benzotriazole, which comprises treating 2-nitro-2'-hydroxy-3',5'-di-tert-amylazobenzene with hydrogen at a temperature in the range of from about 20° C. to about 100° C. and at a pressure in the range of from about 15 psia to about 1000 pounds per square inch (about 1.05 to about 70 kg/cm$^2$) in an organic solvent system containing a water-soluble amine, such as isopropanol/diethylamine or toluene/methanol/diethylamine solution, in the presence of a hydrogenation catalyst comprising molybdenum-promoted Raney nickel, and recovering the desired 2-(2-hydroxy-3,5-di-tert-amylphenyl)-2H-benzotriazole. Still another embodiment is exemplified where this process is carried out in an organic solvent system consisting essentially entirely of an organic aliphatic or alicyclic amine, such as n-propylamine, or morpholine.

A further specific embodiment of this exemplified in the process for the production of 2-(2-hydroxy-3,5-di-tert-amylphenyl)-2H-benzotriazole, which comprises treating 2-nitro-2'-hydroxy-3',5'-di-tert-amylazobenzene with hydrogen at a temperature in the range of from about 20° C. to about 100° C. and at a pressure in the range of from about 1 atmosphere to about 66 atmosphere in an alkaline aqueous organic solvent system containing a water immiscible organic hydrocarbon material such as Amsco mineral spirits and an alkali metal hydroxide, preferably potassium hydroxide, in the presence of a wetting agent to facilitate intimate contact of the various ingredients in the heterogeneous system and a hydrogenation catalyst comprising molybdenum-promoted Raney nickel, and recovering the desired 2-(2-hydroxy-3,5-di-tert-amylphenyl)-2H-benzotriazole.

Other objects and embodiments will be found in the following, further detailed description of this invention.

The reduction of 2-nitro-2'-hydroxy-5'-methylazobenzene was carried out in an aqueous alkaline solution employing sufficient sodium hydroxide to convert the waterinsoluble azobenzene intermediate into the corresponding water-soluble sodium phenolate salt. A hydrogenation catalyst comprising molybdenum-promoted Raney nickel was used and the reduction and cyclization effected at a hydrogen pressure of from about 15 psia to about 85 pounds per square inch (about 1.05 to about 5.85 kg/cm$^2$, about 1 to about 5.7 atmospheres) at temperatures from about 20° C. to about 100° C., with a recovery of pure product in yields in the order of up to 77%. However, higher pressures up to about 1000 pounds per square inch (about 70 kg/cm$^2$, 66 atmospheres) may also be used with equivalent results.

While many of the 2-nitro-2'-hydroxyazobenzene intermediates useful in this invention have such a combination of chemical and physical properties that they can be converted in strong aqueous alkaline solution into the corresponding water-soluble alkali phanolate salts, other 2-nitro-2'-hydroxyazobenzene intermediates because of their more hydrocarbon nature remain essentially insoluble in these strong aqueous alkaline solutions. In order to facilitate the required close proximity of the catalyst, hydrogen and o-nitroazobenzene intermediate in this heterogeneous reaction, the use of a wetting or dispersing agent is required.

In the process according to the invention the 2-nitro-2'-hydroxyazobenzenes insoluble in strong aqueous alkaline solution are employed as dispersions in water. The term dispersion is used in the present invention to describe any fine distribution of the 2-nitro-2'-hydroxyazobenzenes. Dispersions are produced by adding dispersing agents to the aqueous alkali and the appropriate 2-nitro-2'-hydroxyazobenzene compound mixture in a concentration between 0.1% and 5% by weight, and preferably between 0.5% and 3% by weight, of the dispersing agent. It is frequently necessary to stir very rapidly at the same time. This rapid stirring should be maintained after addition of the promoted-nickel catalyst and during the hydrogenation reaction itself to maximize contact between the various components of this heterogeneous system.

Examples of dispersing agents which can be used according to the inventions are dispersing agents from the following list [Ullmann, Encyklopaedie der Technischen Chemie (Encyclopedia of Industrial Chemistry), Third Edition, Volume 16, 1965, pages 724–741] which is incorporated by reference.

In the case of the anionic surface-active agents, the anion is shown. The cation is generally an alkali metal ion. In the case of the cationic surface-active agents, the cation is shown. The anion is generally a chloride or methosulfate ion.

In this list below, the symbols denote the following:
R denotes a long-chain alkyl radical,
R' denotes a short alkyl radical or H, and
X denotes an alkylene radical, for example —(CH$_2$)$_n$—, with n=1–3.

---

Aionic surface-active agents a) Salts of carboxylic acids

R—COO$^-$   Soaps
R—CONH—X—COO$^-$

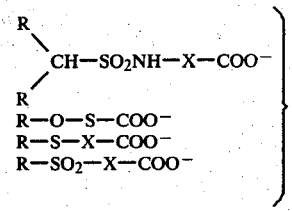

R—O—S—COO$^-$
R—S—X—COO$^-$   Modified soaps with intermediate members
R—SO$_2$—X—COO$^-$ b) Sulfuric acid esters   Sulfated oils and fatty acids

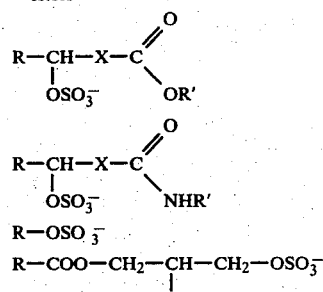   Sulfated esters

Sulfated amides

R—OSO$_3^-$
R—COO—CH$_2$—CH—CH$_2$—OSO$_3^-$   Sulfated fatty acid monoglycerides and others
                  |
                  OH
R—CONH—X—OSO$_3^-$   Sulfated fatty acid alkyloamides
R—O—X—OSO$_3^-$   Sulfated ethers c) Alkylsulfonates R—CH—R'   Simple alkylsulfonates
   |
   SO$_3^-$ CH$_2$—COOR   Sulfosuccinic acid esters
$^-$O$_3$S—CH—COOR

RCOO—X—SO$_3^-$
R—CON—X—SO$_3^-$
     |
     R'

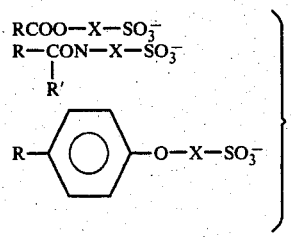   Alkylsulfonates with intermediates members d) Alkylarylsulfonates

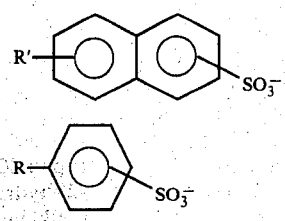   Alkylnapthalenesulfonates

Alkylbenezenesulfonates e) Surface-active agents with less customary anionic groups

| | |
|---|---|
| 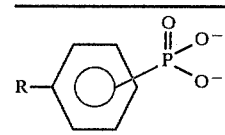 | Alkylphosphates (various kinds) |
| | Salts of alkylbenzenephosphonic acids |
| Cationic surface-active agents | |
| a) Amine salts | |
| $R{-}\overset{+}{N}H_3$ | |
| $R{-}\overset{+}{N}H_2{-}R'$ | Primary, secondary and tertiary amine salts |
| $R{-}\overset{+}{N}H{-}R'$<br>$\quad\;\;\vert$<br>$\quad\;\;R'$ | |
| $R{-}COO{-}X{-}\overset{+}{N}HR'_2$ | Primary, secondary and tertiary amine salts with intermediate members |
| $R{-}CONH{-}X{-}\overset{+}{N}HR'_2$<br>$R{-}O{-}X{-}\overset{+}{N}HR'_2$ | |
| b) Quaternary ammonium salts | |
| $\quad\;\;R'$<br>$\quad\;\;\vert$<br>$R{-}N^+{-}R'$<br>$\quad\;\;\vert$<br>$\quad\;\;R'$ | (Also with intermediate members, as in the case of amine salts) |
| c) Phosphonium salts | d) Sulfonium salts |
| $\quad\;\;R'$<br>$\quad\;\;\vert$<br>$R{-}P^+{-}R'$ and<br>$\quad\;\;\vert$<br>$\quad\;\;R'$ | $\quad\;\;R'$<br>$\quad\;\;\vert$<br>$R{-}S^+$<br>$\quad\;\;\vert$<br>$\quad\;\;R'$ |
| Amphoteric surface-active agents | |
| $\quad\;\;R'$<br>$\quad\;\;\vert$<br>$R{-}N^+{-}X{-}COO^-$<br>$\quad\;\;\vert$<br>$\quad\;\;R'$ | Betaines |
| $\quad\;\;R'$<br>$\quad\;\;\vert$<br>$R{-}N^+{-}X{-}SO_3^-$<br>$\quad\;\;\vert$<br>$\quad\;\;R'$ | |
| $\quad\;\;R'$<br>$\quad\;\;\vert$<br>$R{-}N^+{-}X{-}O{-}SO_3^-$<br>$\quad\;\;\vert$<br>$\quad\;\;R'$ | Sulfate-betaines |
| Non-ionic surface-active agents | |
| a) Ethylene oxide adducts | |
| $R{-}(O{-}CH_2{-}CH_2)_n{-}OH$ | Alkyl-polyethylene glycols |
| $-(O{-}CH_2{-}CH_2)_n{-}OH$ | Alkylphenyl-polyethylene glycols |
| $R{-}CO(O{-}CH_2{-}CH_2)_n{-}OH$ | Acyl-polyethylene glycols |
| $H{-}(O{-}CH_2{-}CH_2)_n{-}(O{-}CH{-}CH_2)_m{-}(O{-}CH_2CH_2)_n{-}OH$<br>$\qquad\qquad\qquad\qquad\qquad\;\;\vert$<br>$\qquad\qquad\qquad\qquad\qquad CH_3$ | Oxethylated poly-propylene glycols |
| b Further non-ionic surface-active agents | |
| $R{-}COO{-}CH_2{-}CH{-}CH_2{-}OH$<br>$\qquad\qquad\qquad\;\;\vert$<br>$\qquad\qquad\qquad OH$ | Fatty acid monoglycerides |
| $R{-}COO{-}C_6H_{11}O_4$ | Anhydrous sorbitol mono-fatty acid esters |
| $R{-}CONH{-}X{-}OH$<br>$R{-}CON{-}X{-}OH$<br>$\quad\;\;\diagdown$<br>$\qquad X{-}OH$ | Fatty acid alkyloamides |
| $R{-}COO{-}C_{12}H_{21}O_{10}$ | Sucrose mono-fatty acid esters |

Effective dispersing agents are found in the cationic, anionic and non-ionic compound classes. Among the preferred dispersing agents are long chain amines, amine salts of long chain acids, alkyl polyethylene glycols, alkylphenyl polyethylene glycols, polyhydroxyalkyl monoesters of fatty acids and the like. The following may be mentioned as illustrative examples: sorbitan monooleate, sorbitol monooleate, lauryl polyethylene glycol, p-dodecylphenyl polyethylene glycol, octadecylamine salts, diethanolamine salts of myristic acid and the like. Particularly effective as wetting agents were the polyhydroxyalkyl monoesters of fatty acids such as sorbitan monooleate (Span 80).

The reduction of 2-nitro-2'-hydroxy-5'-methylazobenzene was carried out in an alkaline aqueous isopropanol solution employing sufficient sodium hydroxide to convert the water-insoluble azobenzene intermediate into the corresponding water-soluble sodium phenolate salt. A hydrogenation catalyst comprising molybdenum-promoted Raney nickel was used and the reduction and cyclization effected at a hydrogen pressure of from about 15 psia to about 85 pounds per square inch absolute (about 1.05 to about 5.85 kg/cm$^2$, about 1 to about 5.7 atmospheres) at temperatures from about 20° C. to about 100° C., with a recovery of pure product in yields in the order of up to 80%. However, higher pressures up to about 1000 pounds per square inch (about 70 kg/cm$^2$, 66 atmospheres) may be used with equivalent results.

The reduction of 2-nitro-2'-hydroxy-3',5'-di-tert-amylazobenzene was carried out in an isopropanol/diethylamine solution with a hydrogenation catalyst comprising molybdenum-promoted Raney nickel. The reduction and cyclization was effected at a hydrogen pressure of from about 15 psia to about 85 pounds per square inch absolute (about 1.05 to about 5.85 kg/cm$^2$, about 1 to about 5.7 atmospheres) at temperatures from about 20° C. to about 100° C., with a recovery of pure product in yields in the order of up to 78%. However, higher pressures up to about 1000 pounds per square inch (about 70 kg/cm$^2$, 66 atmospheres) may also be used with equivalent results. Using the same conditions noted above, the reduction of 2-nitro-2'-hydroxy-5'-methylazobenzene was carried out in a toluene/methanol/diethylamine solution with a hydrogenation catalyst comprising molybdenum-promoted Raney nickel with a recovery of pure product in yields in the order of up to 85-90%.

The preferred catalysts which are employed in the process of this invention for effecting the reduction of o-nitroazobenzenes to form 2-aryl-2H-benzotriazoles comprise promoted nickel catalysts.

While nickel hydrogenation catalysts are generally useful in this reaction, some such catalysts are more selective than others. Unpromoted Raney nickel is an effective catalyst in the cyclic reduction of the 2-nitroazobenzene intermediates of this invention, but unless care is taken to control the amount of hydrogen absorbed, excessive hydrogenation can occur with normal Raney nickel to yield undesired by-products of the desired 2-aryl-2H-benzotriazoles.

Fortunately, it was found that selectivity of the nickel catalysts can be favorably affected by the use of certain promoters. A molybdenum-promoted Raney nickel, available as a 50% aqueous slurry as Raney No. 30 from W. R. Grace, is particularly effective in catalyzing the reductive cyclization of the substituted o-nitroazobenzenes to the corresponding 2-aryl-2H-benzotriazoles in high yields and purity in alkaline systems. Small amounts of catalyst are required to effect the desired reaction with quantities of molybdenum-promoted Raney nickel as low as 0.01 mole to 0.03 mole/mole of o-nitroazobenzenes to be reduced being used. More catalyst can be used, but using amounts over 0.5 mole/mole of the o-nitroazobenzene is generally neither needed nor economically attractive.

While Raney nickel promoted by molybdenum is particularly preferred as a catalyst in the process of this invention, other metals are also useful in promoting Raney nickel to being a catalyst for this process although not necessarily with equivalent results. Among such promoters are chromium, zirconium, iron, copper and silver. Chromium-promoted Raney nickel gave results nearly equivalent to those obtained with molybdenum-promoted catalyst in some cases.

Using these promoted nickel catalysts, reduction of the o-nitroazobenzenes to the corresponding N-oxy derivatives goes readily, but the subsequent reduction to the 2-aryl-2H-benzotriazoles is considerably more difficult. Therefore to carry out the process of this invention in a practical fashion, it is often expedient, but not essential, to add roughly half of the total catalyst used as fresh catalyst at the start of the reduction of the N-oxy derivatives, i.e., halfway through the total reaction cycle.

As hereinbefore stated, the reduction is effected at reducing conditions including a temperature within the range of from about 20° C. to about 100° C., a pressure ranging from about 15 psia to about 1000 pounds per square inch absolute (about 1.05 to about 70 kg/cm$^2$, about 1 to about 66 atmospheres) and with sufficient aqueous alkaline solution to convert the hydroxy-substituted o-nitroazobenzenes into their corresponding water-soluble or water-dispersed alkaline phenolate salts. The water-soluble alkaline phenolate salts are prepared by adding the appropriate hydroxy-substituted o-nitroazobenzene to an aqueous alkaline solution of sodium hydroxide, potassium hydroxide, lithium hydroxide, sodium carbonate, potassium carbonate, ammonia or the like. The preferred alkaline solution comprises from about 5 to about 15% by weight sodium hydroxide in water. When using this aqueous alkaline solution, it is possible at the end of the reduction and cyclization reaction to remove the molybdenum-promoted Raney nickel catalyst by filtration for further recycling if desired while leaving the desired 2-aryl-2H-benzotriazole product in aqueous solution as its alkaline salt in the case of the water-soluble salts.

In the case of the water-dispersed alkaline phenolate salts, it is necessary to have an appropriate dispersing agent also present in the system. In these cases the recovery of the catalyst requires precipitation of the crude 2-aryl-2H-benzotriazole product, separation by filtration of the crude product contaminated by the molybdenum-promoted Raney nickel catalyst, dissolving the crude product in an organic solvent such as toluene, xylene, petroleum mineral spirits, cyclohexane, hexane, chlorobenzene, ethylene dichloride, and the like and isolation of the molybdenum-promoted Raney nickel catalyst by filtration. The crude product now in organic solution is extracted with warm mineral acid such as 70% sulfuric acid and then recrystallized by conventional procedures.

A particularly preferred system involves the reduction of a 2-nitroazobenzene whose alkaline phenolate salt is water insoluble by dispersing the potassium phenolate salt in a medium comprising aqueous potassium hydroxide and a water immiscible hydrocarbon such as Amsco mineral spirits in the presence of a wetting agent such as sorbitan monooleate and a molybdenum-promoted Raney nickel catalyst.

As hereinbefore stated, the reduction may also be effected at reducing conditions including a temperature within the range of from about 20° C. to about 100° C., a pressure ranging from about 15 psia to about 100 pounds per square inch (about 1.05 to about 70 kg/cm$^2$, about 1 to about 66 atmospheres) and with sufficient aqueous alkali/alkanol solution to convert the hydroxy-substituted o-nitroazobenzenes into their corresponding soluble alkaline phenolate salts. The soluble alkaline phenolate salts are prepared by adding the appropriate hydroxy-substituted o-nitroazobenzene to an aqueous alkali/alkanol solution containing sodium hydroxide, potassium hydroxide, lithium hydroxide, sodium carbonate, potassium carbonate, ammonia or the like with an alcohol. Any water-miscible alcohol can be used such as methanol, ethanol, isopropanol, methyl cellosolve, n-butanol and the like. For reasons of economics, ease of operation and availability, isopropanol is preferred. The alkali/alkanol solutions preferably comprise a mixture of sodium hydroxide/water/isopropanol in a ratio by weight of from about 30/1000/30 to about 70/340/300 and preferably of from about 60/340/300 to about 60/440/200 for approximately each mole of the o-nitroazobenzene reduced. When using this aqueous alkali/alkanol solution, it is possible at the end of the reduction and cyclization reaction to remove the catalyst by filtration for further recycling if desired while leaving the desired 2-aryl-2H-benzotriazole product in solution as its alkaline salt.

Although a preferred solvent system for many of the 2-aryl-2H-benzotriazoles of this invention is aqueous alkali/isopropanol, other water-miscible organic solvents can also be used advantageously in this process. Such water-miscible organic solvents include ethers such as dioxane, tetrahydrofuran, 1,2-dimethoxyethane, 1,2-diethoxyethane and the like, such solvents are particularly effective in aiding in dissolving the more difficultly soluble hydroxy-substituted o-nitroazobenzenes and their corresponding alkaline phenolate salts where the substituents $R_1$, $R_2$, $R_3$, $R_4$ and $R_5$ tend to deter facile solubility in the alkaline aqueous organic media of this process.

In another variation of this process, the inorganic alkali used to prepare the aqueous alkali solutions used in the alkaline aqueous organic media of this invention may be replaced by water-miscible organic amines. Such amines not only provide the alkaline ambience needed for the reductive cyclization of the o-nitroazobenzenes to the corresponding 2-aryl-2H-benzotriazoles, but also aid in the dissolving of the more difficultly soluble members of said o-nitroazobenzenes and said 2-aryl-2H-benzotriazoles in the reaction media. Thus, the alkaline aqueous organic medium useful in this invention may comprise water containing a water-miscible organic amine in the presence or absence of a water-miscible alkanol or ether described previously. Such water-miscible amines may include primary, secondary or tertiary aliphatic amines with alkyl groups of 1 to 4 carbon atoms, morpholine, piperidine, piperazine, guanidine, pyrrolidine, and the like. The simple aliphatic amines are preferred such as diethylamine or n-propylamine.

As hereinbefore stated, the reduction may be perticularly well effected at reducing conditions including a temperature within the range of from about 20° C. to about 100° C., a pressure ranging from about 15 psia to about 1000 pounds per square inch (about 1.05 to about 70 kg/cm$^2$, about 1 to about 66 atmospheres) wherein the o-nitroazobenzene intermediate being reduced is dissolved in an organic alkaline medium. Such a medium may comprise a water-miscible alkanol and/or ether plus an organic amine, a hydrocarbon plus an organic amine or a hydrocarbon plus a water-miscible alkanol and/or ether plus an organic amine.

Water-miscible alcohols of use in this invention include methanol, ethanol, isopropanol, methyl cellosolve (2-methoxyethanol), n-butanol and the like. When an alkanol is used alone with an organic amine, for reasons of economics, ease of operation and availability, isopropanol is preferred. The concentration of the o-nitroazobenzene being hydrogenated in the alcohol, such as isopropanol, ranges from 15% to 30% by weight.

Other water-miscible organic solvents can also be used advantageously in combination with an organic amine. Such water-miscible solvents include ethers such as dioxane, tetrahydrofuran, 1,2-dimethoxyethane, 1,2-diethoxyethane and the like.

Mixtures of water-miscible alcohols and ethers can also be used in this process along with an organic amine.

Other solvents found useful in this process include the trialkyl phosphates such as triethyl phosphate, tributyl phosphate and the like.

In another modification of the solvent system operable with the present process, the o-nitroazobenzene intermediate may be dissolved in a hydrocarbon solvent, with or without the presence of a water-soluble alcohol or ether, containing a water-soluble organic amine. The hydrocarbon solvents may be aromatic, such as benzene, toluene, xylene and the like, cyclohexane, aliphatic, such as hexane, heptane, and the like, petroleum mineral spirits, medium fraction petroleum ether and other related petroleum solvents and mixtures thereof. A particularly useful solvent combination is toluene containing about 25 to 35% by weight methanol.

The concentration by weight of o-nitroazobenzene intermediate used in any of the solvent systems of this invention can range from dilute solutions in the range of 5–10% to concentrated solutions in the range of 20–30%. For reasons of economy, the more concentrated solutions are preferred.

Another critical part of the solvent system is ammonia or an organic amine in order to provide a strongly alkaline milieu in which the reductive cyclization reaction can occur. From 1.0 to 3.0 moles of amine/mole of the o-nitroazobenzene, preferably from 1.5 to 2.5 moles of amine/mole of the o-nitroazobenzene and most preferably from 1.7 to 2.2 moles of amine/mole of o-nitroazobenzene being reduced are required. Any organic, strongly alkaline amine can be used. It is preferred to use water-miscible amines such as primary, secondary or tertiary aliphatic amines with alkyl groups of 1 to 6 carbon atoms, n-butylamine, isopropylamine, pyrrolidine, piperazine, guanidine, morpholine piperidine and the like. It is preferable that the amine used form a water-soluble hydrochloride or sulfate salt in order to facilitate the separation of the amine component from the organic solution of the desired 2-aryl-2H-benzotriazole and to aid in the isolation of a pure desired product from said solution. The amine is regenerated from its acid salt and recycled in the reaction system. For reasons of economics, ease of operation and availability, morpholine, piperidine and the lower dialkylamines, such as diethylamine, dimethylamine, di-n-propylamine and the like are preferred. Particularly preferred is diethylamine or n-propylamine.

While the reduction cyclization reaction does not occur in the absence of a strong alkaline milieu such as is provided by one or more of the organic amines described above, it is often expedient to run the instant process where the organic solvent consists essentially entirely of one of the organic amines alone. In such a case, an excess molar quantity of amine relevant to the o-nitroazobenzene is always present. This solvent system has the advantage of simplified solvent recovery at the end of the reaction since mixtures of solvents are not involved. Amines providing a particularly good balance of base strength, solvent character, physical properties, ease of handling, availability and operability in the instant process included n-propylamine, diethylamine, triethylamine, isopropylamine, n-butylamine, dibutylamine, tert-butylamine, amylamine, morpholine and the like. Using an organic amine as the organic solvent for this process, yields in the order of 70 to 90% can be obtained.

Isolation of a product in good yield and acceptable purity is another feature of this invention. The aqueous alkali or alkaline aqueous organic solution of the desired hydroxy-substituted 2-aryl-2H-benzotriazole salt, preferably the sodium salt, is acidified with aqueous mineral acid, preferably sulfuric acid or hydrochloric acid, to a pH of 10 or below in order to precipitate the desired hydroxy-substituted 2-aryl-2H-benzotriazole as a crude product in yields in the range of 75 to 90%. The crude product may be further purified by one of several procedures to give purified products of high purity in yields in the range of 70 to 80%. A variety of trace by-products are formed during the reduction of o-nitroazobenzenes. These include the corresponding o-aminoazobenzenes, o-aminohydrazobenzenes, o-phenylenediamine, anilines, aminophenols and 1,2,3-benzotriazoles. Most of these by-product impurities are removed by an acid, preferably sulfuric acid, wash followed by an alcohol, preferably isopropanol, wash and finally a water wash of crude 2H-benzotriazole product. Alternatively, the crude product may be dissolved in an organic solvent, such as toluene, and the impurities extracted by an aqueous acid solution, and the product isolated then from organic solution by conventional procedures.

Isolation of a product in good yield and high purity is a particularly important feature of this invention when an alkaline organic solution of the desired hydroxy-substituted 2-aryl-2H-benzotriazole is extracted with sufficient aqueous mineral acid, preferably sulfuric acid or hydrochloric acid, to remove the amine and most impurities formed during the reaction. A variety of trace by-products are formed during the reduction of o-nitroazobenzenes. These include the corresponding o-aminoazobenzenes, o-aminohydrazobenzenes, o-phenylenediamine, anilines, aminophenols and 1,2,3-benzotriazoles. Most of these by-product impurities are removed by an acid, preferably hydrochloric or sulfuric acid, wash. An advantage of this process lies in the fact that the desired product dissolved in the organic solvent, preferably isopropanol/diethylamine or toluene/methanol/diethylamine, can be separated from most impurities and the diethylamine by the aforementioned aqueous acid wash leaving the product dissolved in isopropanol or toluene. The isolation of a pure product generally requiring no further purification for commercial use is carried out by conventional crystallization procedures in yields in the range of 65 to 85%.

The process of this invention may be effected in any suitable manner and may comprise either a batch or continuous type of operation. For example, when a batch-type operation is used, a quantity of the hydroxy-substituted o-nitroazobenzene, water, sufficient alkali, such as sodium hydroxide, to prepare the water-soluble or water-dispersed alkaline phenolate salt along with the molybdenum-promoted Raney nickel catalyst and dispersing agent if needed is placed in an appropriate apparatus such as a shaking or stirred autoclave. Hydrogen is pressurized in until the desired initial pressure is reached. The autoclave and the contents thereof are then heated, if needed, to the desired reaction temperature and maintained thereat with agitation until about half the theoretical amount of hydrogen is absorbed, whereupon an additional amount of fresh molybdenum-promoted Raney nickel catalyst is added to the autoclave. The reaction is then continued until slightly more than the theoretical amount of hydrogen is absorbed and the reduction reaction is complete. At the end of this time, the excess pressure is vented, the aqueous alkaline solution, usually warm, is subjected in the case of the water-soluble alkaline phenolate salts to filtration, preferably under an inert atmosphere such as nitrogen or argon, to remove the catalyst. The solution is then brought to room temperature and treated with mineral acid solution to precipitate the desired hydroxy-substituted 2-aryl-2H-benzotriazole crude product, which may be optionally further purified by treatment with aqueous acid and recrystallization from an organic solvent.

In the case of the water-dispersed alkaline phenolate salts, the mixture is just brought to room temperature and neutralized with mineral acid solution. The insoluble hydroxy-substituted 2-aryl-2H-benzotriazole crude product containing therein the molybdenum-promoted Raney nickel catalyst residue is then dissolved in a solvent, such as toluene. The solution of the crude product is then filtered to remove the catalyst residue and the crude product is further purified as described above.

The process of this invention may also be effected in a similar batch operation wherein the quantity of hydroxy-substituted o-nitroazobenzene is converted to its corresponding alkaline phenolate salt by dissolving in an alkaline aqueous organic medium, preferably in aqueous sodium hydroxide and isopropanol. The process is thereafter carried out as described above for alkaline phenolate salts dissolved in an aqueous alkaline solution.

In another batch operation, a quantity of the hydroxy-substituted o-nitroazobenzene, alkanol, such as isopropanol, amine, such as diethylamine, along with the catalyst, such as molybdenum-promoted Raney nickel, is placed in appropriate apparatus such as a shaking or stirred autoclave. In other cases the organic solvent will comprise a hydrocarbon solvent, such as toluene or mineral spirits, a water-soluble alkanol, such as methanol, and an amine, such as diethylamine. Hydrogen is pressurized in until the desired initial pressure is reached. The autoclave and the contents thereof are then heated, if needed, to the desired reaction temperature and maintained thereat with agitation until about half the theoretical amount of hydrogen is absorbed, whereupon an additional amount of fresh molybdenum-promoted Raney nickel catalyst is added to the autoclave. The reaction is continued until slightly more than the theoretical amount of hydrogen is taken up and the reduction reaction is complete. At the end of this time the excess pressure is vented, the warm alkaline organic solution is subjected to filtration, preferably under an inert atmosphere such as nitrogen or argon, to remove the catalyst. The solution, still warm, is extracted with mineral acid solution to remove impurities and the diethylamine to leave the desired hydroxy-substituted 2-aryl-2H-benzotriazole product in organic solution from which it may be isolated in pure form by crystallization.

It is also contemplated within the scope of this invention that the preparation of the 2-aryl-2H-benzotriazoles by the reduction and cyclization of o-nitroazobenzenes may also be effected in a continuous manner, although not necessarily with equivalent results. For example, when a continuous type operation is used, the hydroxy-substituted o-nitroazobenzene starting material is premixed with, and dissolved or dispersed in an alkaline medium, said solution or dispersion fed continuously to a reaction zone which is maintained at the proper operating conditions of temperature and pressure and which contains the hydrogenation catalyst. Means are provided to add additional catalyst before the second half of the reaction cycle.

Hydrogen is pressurized into the reaction zone by a separate means. After desired residence time, the reactor effluent is continuously discharged and the effluent solution is acidified to isolate the desired product. Due to the nature of the catalyst employed, a particularly effective continuous type of operation comprises a fixed bed of catalyst subjected to either an upward or downward flow of the reaction solution or dispersion. If it is desirable to carry out the reduction as a two-step process with a different operating temperature for each step, two reaction zones in series each operating at the preferred temperature range for the specific reduction step involved may be used.

The reduction of o-nitroazobenzenes to the corresponding 2-aryl-2H-benzotriazoles is a two-step process as outlined below.

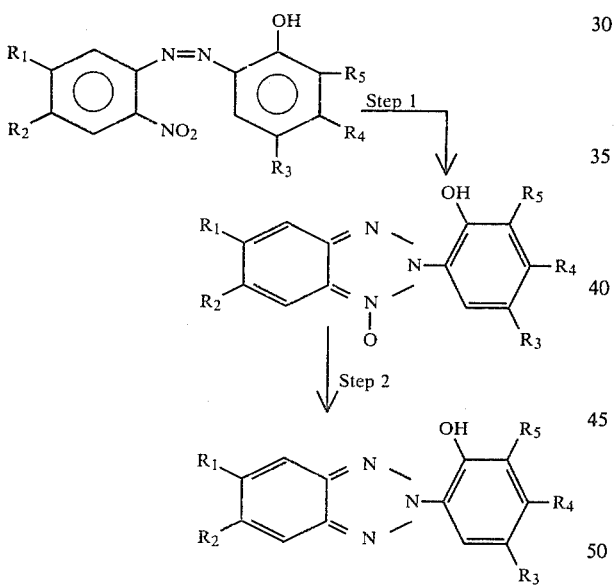

Step 1—The reduction of the o-nitroazobenzene to the N-oxybenzotriazole derivative proceeds rapidly and exothermically even at low temperature under the process conditions of this invention.

Step 2—The reduction of the N-oxybenzotriazole intermediate to the corresponding 2-aryl-2H-benzotriazole product goes more slowly. This reduction can be greatly expedited by adding more catalyst, raising the temperature, increasing the hydrogen pressure or by combination of these factors.

Generally, the reaction ceases when the N-oxy intermediate is completely reduced to the corresponding 2-aryl-2H-benzotriazole making for facile control of this catalytic hydrogenation process. However, with some highly substituted benzotriazoles, reduction should be stopped when the appropriate amount of hydrogen has been absorbed and reacted to prevent further reductive cleavage of the desired 2-aryl-2H-benzotriazoles prepared.

Specifically, the instant invention provides an improved process for production of compounds having the formula I

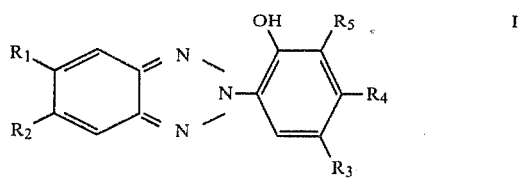

wherein
$R_1$ is hydrogen or chlorine,
$R_2$ is hydrogen, chlorine, lower alkyl of 1 to 4 carbon atoms, lower alkoxy of 1 to 4 carbon atoms, carboalkoxy of 2 to 9 carbon atoms, carboxy or $-SO_3H$,
$R_3$ is alkyl of 1 to 12 carbon atoms, alkoxy of 1 to 4 carbon atoms, phenyl, phenyl substituted with alkyl groups, said alkyl groups having 1 to 8 carbon atoms, cycloalkyl of 5 to 6 carbon atoms, carboalkoxy of 2 to 9 carbon atoms, chlorine, carboxyethyl or arylalkyl of 7 to 9 carbon atoms,
$R_4$ is hydrogen, lower alkyl of 1 to 4 carbon atoms, lower alkoxy of 1 to 4 carbon atoms, chlorine or hydroxyl, and
$R_5$ is hydrogen, alkyl of 1 to 12 carbon atoms, chlorine, cycloalkyl of 5 to 6 carbon atoms or arylalkyl of 7 to 9 carbon atoms.

$R_2$ can be lower alkyl of 1 to 4 carbon atoms such as methyl, ethyl or n-butyl. $R_2$ can also be lower alkoxy of 1 to 4 carbon atoms such as methoxy, ethoxy or n-butoxy. $R_2$ can also be carboalkoxy of 2 to 9 carbon atoms such as carbomethoxy, carboethoxy, or carbo-n-octoxy.

$R_3$ can be alkyl of 1 to 12 carbon atoms such as methyl, ethyl, sec-butyl, tert-butyl, amyl, tert-octyl or n-dodecyl. $R_3$ can also be alkoxy of 1 to 4 carbon atoms such as methoxy, ethoxy or n-butoxy. $R_3$ is also phenyl substituted with alkyl groups, said alkyl groups having 1 to 8 carbon atoms such as methyl, tert-butyl, tert-amyl or tert-octyl. $R_3$ can also be cycloalkyl of 5 to 6 carbon atoms such as cyclopentyl or cyclohexyl. $R_3$ is also carboalkoxy of 2 to 9 carbon atoms such as carbomethoxy, carboethoxy, carbo-n-butoxy or carbo-n-octoxy. $R_3$ is also arylalkyl of 7 to 9 carbon atoms such as benzyl, α-methylbenzyl or α,α-dimethylbenzyl.

$R_4$ can be lower alkyl of 1 to 4 carbon atoms such as methyl, ethyl or n-butyl.

$R_4$ can also be lower alkoxy of 1 to 4 carbon atoms such as methoxy, ethoxy or n-butyloxy.

$R_5$ can be alkyl of 1 to 12 carbon atoms such as methyl, sec-butyl, tert-butyl, tert-amyl, tert-octyl or n-dodecyl.

$R_5$ can also be cycloalkyl of 5 to 6 carbon atoms such as cyclopentyl or cyclohexyl. $R_5$ is also arylalkyl of 7 to 9 carbon atoms such as benzyl, α-methylbenzyl or α,α-dimethylbenzyl.

Preferably $R_1$ is hydrogen.
Preferably $R_2$ is hydrogen, chlorine, lower alkyl of 1 to 2 carbon atoms, methoxy or carboxy.

Preferably R₃ is alkyl of 1 to 12 carbon atoms cyclohexyl, phenyl, chlorine, α-methylbenzyl or carboxyethyl.

Preferably R₄ is hydrogen, hydroxyl or methyl.

Preferably R₅ is hydrogen, chlorine, alkyl of 1 to 12 carbon atoms, cyclohexyl, benzyl or α-methylbenzyl.

Most preferably R₂ is hydrogen or chlorine.

Most preferably R₃ is methyl, tert-butyl, tert-amyl, tert-octyl, sec-butyl, cyclohexyl, chlorine or carboxyethyl.

Most preferably R₄ is hydrogen.

Most preferably R₅ is hydrogen, chlorine, methyl, sec-butyl, tert-butyl, tert-amyl, tert-octyl or α-methylbenzyl.

The process involved the reduction of an o-nitroazobenzene intermediate of the formula II

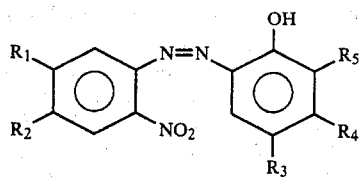

wherein R₁, R₂, R₃, R₄ and R₅ are as described previously.

The starting o-nitroazobenzene intermediates are prepared by coupling the appropriate o-nitrobenzenediazonium compounds of formula III

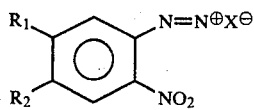

wherein R₁ and R₂ are as described previously and X is chloride, sulfate, or other anionic species, but preferably chloride, with phenols of formula IV

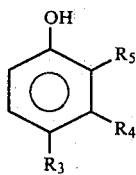

which couple in the ortho position to the hydroxy group.

The o-nitrobenzenediazonium compounds are in turn prepared by standard diazotization procedures using sodium nitrite in acid solution with the corresponding o-nitroanilines of formula V

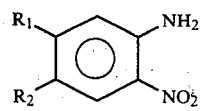

For illustration purposes some specific examples of compounds of formulas IV and V are listed. These items are generally available as items of commerce.

Compounds of Formula IV p-cresol
2,4-di-tert-butylphenol
2,4-di-tert-amylphenol
2,4-di-tert-octylphenol
2-tert-butyl-4-methylphenol
4-cyclohexylphenol
4-tert-butylphenol
4-tert-amylphenol
4-tert-octylphenol
2,4-dimethylphenol
3,4-dimethylphenol
4-chlorophenol
2,4-dichlorophenol
3,4-dichlorophenol
4-phenylphenol
4-phenoxyphenol
4-o-tolylphenol
4-(4'-tert-octyl)phenylphenol
ethyl 4-hydroxybenzoate
n-octyl 4-hydroxybenzoate
4-methoxyphenol
4-n-octylphenol
4-n-dodecylphenol
resorcinol
4-(α-methylbenzyl)phenol
2-(α-methylbenzyl)-4-methylphenol
2-cyclohexyl-4-methylphenol
4-sec-butylphenol
2-sec-butyl-4-tert-butylphenol
2-tert-butyl-4-sec-butylphenol
4-carboxyethylphenol
2-methyl-4-carboxyethylphenol Preferably compounds of formula IV useful in this invention are p-cresol
2,4-di-tert-butylphenol
2,4-di-tert-amylphenol
2,4-di-tert-octylphenol
2-tert-butyl-4-methylphenol
4-tert-octylphenol
4-n-octylphenol
4-n-dodecylphenol
resorcinol
2-sec-butyl-4-tert-butylphenol
2-(α-methylbenzyl)-4-methylphenol Compounds of Formula V o-nitroaniline
4-chloro-2-nitroaniline
4,5-dichloro-2-nitroaniline
4-methoxy-2-nitroaniline
4-methyl-2-nitroaniline
4-ethyl-2-nitroaniline
n-butyl 3-nitro-4-aminobenzoate
n-octyl 3-nitro-4-aminobenzoate
4-n-butoxy-2-nitroaniline
3-nitro-4-aminobenzoic acid
3-nitro-4-aminobenzenesulfonic acid Preferably compounds of Formula V useful in this invention are o-nitroaniline
4-chloro-2-nitroaniline The o-nitroazobenzene intermediates of Formula II where R₁ is chlorine; R₂ is chlorine, lower alkyl of 1 to 4 carbon atoms, lower alkoxy of 1 to 4 carbon atoms, carboalkoxy of 2 to 9 carbon atoms; R₃ is alkoxy of 1 to 4 carbon atoms, phenyl, phenyl substituted with alkyl groups said alkyl groups have 1 to 8 carbon atoms, carboalkoxy of 7 to 9 carbon atoms, arylalkyl of 7 to 9 carbon atoms, alkyl of 4 to 12 carbon atoms; R₄ is alkyl of 1 to 4 carbon atoms, alkoxy of 1 to 4 carbon atoms, chlorine; and $R_5$ is alkyl of 1 to 12 carbon atoms, chlorine, cycloalkyl of 5 to 6 carbon atoms or arylalkyl of 7 to 9 carbon atoms generally exhibit poor solubility in aqueous alkaline solution. With such intermediates the use of the dispersing or wetting agents described previously is generally necessary in the process of this invention when an aqueous alkaline medium is employed.

The 2-aryl-2H-benzotriazoles have found wide use as dyestuff intermediates, optical brightener blue fluorescent agents and selective ultraviolet light absorbing stabilizers affording valuable protection for fibers, films and a variety of polymeric structures subject to deterioration by ultraviolet radiation. These materials have become important items of commerce.

The 2-aryl-2H-benzotriazoles are complex organic molecules which require careful synthetic procedures for their production in good yield and acceptable purity.

The present invention is concerned with an improved process to prepare ultraviolet stabilizers which are substituted 2-aryl-2H-benzotriazoles. These are distinguished by a very slight absorption in visible light and very high fastness to light in various substastrates. Particularly valuable members of these stabilizers are compounds having a free hydroxyl group in the 2-position of the aryl group linked to the 2-nitrogen of the benzotriazole and which are further substituted in the 3- and 5- or 4- and 5-positions by lower alkyl groups and may be substituted by a chlorine in the 5-position of the benzotriazole nucleus.

The description, preparation and uses of these valuable substituted 2-aryl-2H-benzotriazoles are further taught in the U.S. Pat. Nos. 3,004,896, 3,055,896, 3,072,585, 3,074,910, 3,189,165 and 3,230,194.

The following examples are given to illustrate the process of the present invention, but are not intended to limit the scope of the present invention in any manner whatsoever.

EXAMPLE 1

2-(2-Hydroxy-3,5-di-tert-amylphenyl)-2H-benzotriazole

To a 1-liter, low pressure hydrogenation reactor were charged under nitrogen with the reactor held at 45° C. by external heating 79.1 grams (0.2 mole) 2-nitro-2'-hydroxy-3',5'-di-tert-amylazobenzene (97% pure) dissolved in a solution of 230 grams of isopropanol and 29.3 grams (0.4 mole) of diethylamine and 3.0 grams of molybdenum-promoted Raney nickel catalyst as a 50% aqueous slurry. This amount of catalyst was about 1.9% based on the azobenzene intermediate. The reactor was flushed several times with hydrogen and then pressurized with hydrogen to 15 psia (1.05 kg/cm², 1 atmosphere). The contents of the reactor were agitated vigorously and hydrogenated at 43°–47° C. until hydrogen uptake slowed, which normally occurred after 50–65% of the theoretical uptake of hydrogen. The hydrogen atmosphere in the reactor was then vented and replaced with nitrogen. An additional amount of 6.0 grams of the molybdenum-promoted Raney nickel catalyst as a 50% aqueous slurry was then added to the reactor. This amount of catalyst was another 3.8% based on the azobenzene intermediate for a total amount of catalyst used of 5.7%. The hydrogen atmosphere was then reimposed on the reactor. The hydrogen uptake again first increased, but eventually ceased when about 114% of the theoretical uptake of hydrogen had occurred. Near the end of the reaction at 45° C., the reaction mixture became thick as crystals appeared in the system. The hydrogenation reaction required about 4 hours for completion.

The hydrogen atmosphere present in the reactor was again vented and replaced with nitrogen. The contents of the reactor were heated to 60°–65° C. to dissolve the crystals present. With agitation continued, 81.5 grams of Amsco mineral spirits were charged to the reactor. The contents of the reactor were then filtered under nitrogen to remove the molybdenum-promoted nickel catalyst dispersed therein. The recovered catalyst was washed on the filter with two portions of 4 grams of isopropanol. This washed catalyst was then suitable for reuse in another hydrogenation reaction.

The filtrate containing the desired product in solution was reheated to 65° C. and then treated with 160 grams of 6% aqueous hydrochloric acid (0.26 mole). The system was stirred for 10 minutes and then allowed to settle for another 10 minutes. The aqueous acidic layer was then separated from the organic solvent layer containing the desired product in solution. The aqueous layer was extracted twice with 30 grams each of Amsco mineral spirits which were added to the organic solvent layer. The combined organic solution was extracted twice again with 40 grams of 6% aqueous hydrochloric acid (0.14 mole).

The Amsco mineral spirit/isopropanol solution of the desired product was then vacuum distilled at 95° C. to remove about ⅔ of the Amsco mineral spirits (about 90 grams). To the residue was added 110 grams of isopropanol and 7 grams of concentrated hydrochloric acid. The mixture was heated to 70° C. to form a homogeneous solution which was then cooled with stirring to 50° C., seeded, held at 45°–50° C. to permit crystallization of the desired product and finally, cooled to 0° C. The desired product, 2-(2-hydroxy-3,5-di-tert-amylphenyl)-2H-benzotriazole was isolated by filtration, washed with six portions of 20 ml each of cold isopropanol and dried in vacuum at 50° C. to yield 54.8 grams (78% of theory) of pure material requiring no further purification for commercial use.

When the above hydrogenation was carried out in a 50% solution of Amsco mineral spirits in isopropanol in the presence of one equivalent of diethylamine to the azobenzene intermediate, the yield of isolated product was 75%.

EXAMPLE 2

2-(2-Hydroxy-3,5-di-tert-amylphenyl)-2H-benzotriazole

To a 10-gallon stainless steel jacketed reactor fitted with a radial turbine agitator, temperature recorder-controller, a hydrogen delivery system so arranged that internal reactor pressure would remain constant throughout the hydrogenation and a nitrogen safety sparging system, was added under nitrogen 10 kg of isopropanol and 1.76 kg (24.0 moles) of diethylamine. The solution was heated to 50° C. and 4.6 kg (12.0 moles) of 2-nitro-2'-hydroxy-3',5'-di-tert-amylazobenzene (97.1% pure) and 3.81 kg of isopropanol were added under nitrogen. The mixture was stirred vigorously and heated to 50° C. for 15 minutes under nitrogen. To the solution was then added 180 grams of a 50% slurry in water of a molybdenum-promoted Raney nickel catalyst (W. R. Grace, Raney No. 30 grade) and 200 ml of isopropanol. This is 2% catalyst based on the o-nitroazobenzene intermediate in solution. The system was pressured with nitrogen and cooled to 45° C. The nitrogen was vented and replaced by hydrogen with a cylinder regulator pressure of 50 pounds per square inch gauge (3.5 kg/cm$^2$). The theoretical hydrogen pressure drop for complete reaction is 178 psi (12.46 kg/cm$^2$).

The agitator speed was set at 400 rpm and the vessel held at 50 psig (3.5 kg/cm$^2$) and 45° C. Reaction was continued until the pressure in the hydrogen cylinder dropped less than 5% of theory per hour or roughly 55 to 70% of the theoretical pressure drop. The first step of the reduction to the corresponding N-oxy compound was complete. This required about 50 minutes.

The reactor was vented, pressurized with nitrogen, stirring stopped and vented again. A second batch of molybdenum-promoted Raney nickel catalyst (360 grams of a 50% slurry in water) and 2000 ml of isopropanol were added. This is 4% catalyst based on the original o-nitroazobenzene intermediate used. The system was again pressurized with nitrogen and then hydrogen to 50 psig (3.5 kg/cm$^2$) as before. The reduction was continued with vigorous agitation until the hydrogen cylinder pressure was constant. This required about 2 hours. The reaction mixture was stirred for another hour before venting and pressurizing with nitrogen.

The system was then heated to 60°-65° C. with stirring for 10 minutes. Agitation was stopped and the catalyst allowed to settle for another 10-15 minutes. To this mixture was added 4.89 kg of Amsco mineral spirits. The mixture was heated to 65° C. and stirred vigorously.

The contents of the reactor were then filtered under 10 psig (0.7 kg/cm$^2$) nitrogen pressure to remove the suspended molybdenum-promoted Raney nickel catalyst. The reactor and filter were washed with two 1.2 kg portions of isopropanol. The combined filtrate contains 17.75 kg of 2-(2-hydroxy-3,5-di-tert-amylphenyl)-2H-benzotriazole as a 21% solution in Amsco mineral spirits/isopropanol. This corresponds to a yield of 3.71 kg of product (100%) or 88% of theory.

The material was isolated from this solution by conventional procedures as a product of high purity in a yield of 78%.

The catalyst recovered from the filter can be used again during the first step reduction of another batch of an o-nitroazobenzene to the corresponding N-oxy-2-aryl-2H-benzotriazole.

EXAMPLE 3

2-(2-Hydroxy-3,5-di-tert-amylphenyl)-2H-benzotriazole

Using the general procedure of Example 1, a number of runs were made to determine the influence of several variables on the preparation of the above noted compound.

In all cases the temperature was 45° C., 2 moles of diethylamine per mole of o-nitroazobenzene intermediate and 6% molybdenum-promoted Raney nickel catalyst were used. With one designated exception, the catalyst was added in two portions of 2% for the first reduction step and 4% for the second step.

| Run | Hydrogen Absorbed % of Theory | Yield Isolated Product % | Purity o-Nitro-Azo-benzene | Hydrogen Pressure Psia (kg/cm$^2$) | Time Reaction Min. |
|---|---|---|---|---|---|
| A | 116 | 78 | 100% (Rcrys.) | 15 (1.05) | 360 |
| B | 116 | 78 | 97% (Tech.) | 15 (1.05) | 360 |
| C | 113 | 78 | 100% | 65-50 (4.2-3.2) | 160 |
| D | 124* | 75 | 100% | 15 (1.05) | 360 |
| E | 110** | 72 | 97% | 15 (1.05) | — |

*Same conditions as Run A except different lot of catalyst used. The different lot of catalyst caused a faster uptake of hydrogen in Run D, but did not significantly change the yield of product.
**Same conditions as Run B except that the catalyst used in Run E was a total of 8% with 6% recycled from Run B. 2% additional fresh catalyst was added at the beginning of the second step in order to increase the reduction rate. Without the fresh catalyst, the reduction of the N-oxy compound was sluggish at the atmospheric pressure.

There was no perceptible advantage of using 100% pure recrystallized o-nitroazobenzene intermediate since excellent yields of desired product were obtained from technical intermediates.

The use of higher hydrogen pressure (65 psia versus 15 psia, 4.2 kg/cm$^2$ versus 1.05 kg/cm$^2$) reduced the time required to carry out the reaction significantly.

EXAMPLE 4

2-(2-Hydroxy-5-methylphenyl)-2H-benzotriazole

To a 500 ml Parr shaker bottle was added 48.7 grams (0.18 mole) of 2-nitro-2'-hydroxy-5'-methylazobenzene (95% pure), 66 grams of toluene, 28 grams of methanol and 26.3 grams (0.36 mole) of diethylamine. The resulting slurry was agitated until dissolved. The flask was then purged with nitrogen and 3.0 grams of a 50% slurry in water of a molybdenum-promoted Raney nickel catalyst (W. R. Grace, Raney No. 30) was carefully added. This is 3.2% catalyst based on the o-nitroazobenzene intermediate. The bottle was placed on the Parr hydrogenation shaker apparatus. The bottle was pressurized first with nitrogen and then several times with hydrogen. The pressure was set at 50 psig (3.5 kg/cm$^2$) and agitation begun. The reaction mixture was heated to 45° C. and the hydrogen absorption began as seen by a drop in hydrogen pressure. After the absorption of hydrogen slowed or stopped with a pressure drop of 14-17 psi (0.98-1.19 kg/cm$^2$), the bottle was vented and a nitrogen atmosphere was reimposed. Another 3 grams of a 50% water slurry of the molybdenum-promoted Raney nickel catalyst was carefully added to the bottle. This is another 3.2% catalyst based on the o-nitroazobenzene intermediate.

The bottle was replaced on the Parr shaker and a hydrogen atmosphere reimposed at 50 psig (3.5 kg/cm$^2$). The reaction mixture was then heated to 58°-60° C. The hydrogen pressure was maintained between 50 and 40 psig (3.5 and 2.8 kg/cm$^2$) throughout the second step reduction until the hydrogen absorption levels off. The total drop in hydrogen pressure was 31-33 psi (2.17-2.31 kg/cm$^2$). The total reaction time was 150-175 minutes. The system was vented and a nitrogen atmosphere reimposed for all subsequent steps.

40 Grams of toluene was added to the reaction mixture which was then heated to 70° C. to assure complete solution of the desired product. The reaction mixture was filtered to remove the suspended nickel catalyst which could be recycled in another hydrogenation run after washing with 40 grams of toluene, 40 grams of methanol and finally water. The toluene and methanol washes were combined with the original filtrate. The toluene and methanol were removed by vacuum distillation at 60°–65° C. using a thin film evaporator to yield a thick slurry, 100 grams of methanol was added to the slurry which was agitated until uniform. The slurry was held at 0°–5° C. for 30 minutes and then filtered to yield 37.2 grams (91.9%) of crude product after being washed with 100 grams of methanol and dried.

The use of an equivalent amount of n-propylamine substituted for the diethylamine gave the above named product in an isolated yield of 88%.

EXAMPLE 5

2-(2-Hydroxy-5-methylphenyl)-2H-benzotriazole

Using the procedure of Example 4, 48.7 grams (0.18 mole) of 2-nitro-2'-hydroxy-5'-methylazobenzene (95% pure) was dissolved in 125 grams of water and 16.2 grams of 50% sodium hydroxide solution (0.202 mole). After purging with nitrogen, 3.0 grams of a 50% slurry in water of a molybdenum-promoted Raney nickel catalyst (W. R. Grace Raney No. 30) was carefully added. This is 3.2% catalyst based on the o-nitroazobenzene intermediate. At the end of the first step of the hydrogenation after a hydrogen pressure drop of 14–16 psi (0.98–1.12 kg/cm$^2$), an additional 3.0 grams of catalyst described above was added. The total amount of catalyst used for both steps of the hydrogenation was 6.4% based on the o-nitroazobenzene intermediate used.

The total hydrogen absorption was seen by a hydrogen pressure drop of 35–38 psi (2.45–2.66 kg/cm$^2$) and the total reaction time was 290–340 minutes.

After the hydrogen was vented, a nitrogen atmosphere was reimposed and an additional 3.72 grams of 50% sodium hydroxide solution was added to insure complete solution of the desired product. The suspended catalyst was removed by filtration at 50° C. with the catalyst being washed with 15 grams of 10% sodium hydroxide solution and the 15 grams of water. The catalyst could be used in another hydrogenation run after further washing.

The combined filtrates were treated under a nitrogen atmosphere with a 70% aqueous sulfuric acid solution until the pH was reduced to a value of 10. The crude product which precipitated was isolated by filtration and washed sucessively with 100 ml portions of water, isopropanol and again water. The product was dried in vacuo at 45°–50° C. and was recovered in a yield of 24.9 grams (62% of theory). The product could be further purified by conventional recrystallization procedures.

When 0.5% by weight of the wetting agent sorbitan monooleate, Span 80, was added to the hydrogention system, the above named product was obtained in an yield.

EXAMPLE 6

2-(2-Hydroxy-5-methylphenyl)-2H-benzotriazole

When using the procedure of Example 5, 48.7 grams (0.18 mole) of 2-nitro-2'-hydroxy-5'-methylazobenzene (95% pure) was dissolved in a solution of 9 grams of sodium hydroxide in 30 grams of water and 45 grams of isopropanol, and a total of 7.0 grams of a 50% slurry in water of molybdenum-promoted Raney nickel catalyst (W. R. Grace Raney No. 30) were added in two equal 3.5 grams portions at the start and at the half way point of the hydrogenation, the product, 2-(2-hydroxy-5-methylphenyl)-2H-benzotriazole was obtained in very high yield after removal of the suspended nickel catalyst by filtration and acidification of the filtrate to a pH value of less than 4 using aqueous sulfuric acid.

EXAMPLE 7

2-(2-Hydroxy-5-tert-octylphenyl)-2H-benzotriazole

When using the procedure of Example 1 an equivalent amount of 2-nitro-2'-hydroxy-5'-tert-octylazobenzene is substituted for 2-nitro-2'-hydroxy-3',5'-di-tert-amylazobenzene, the above noted product is obtained.

EXAMPLE 8

5-Chloro-2-(2-hydroxy-3,5-di-tert-butylphenyl)-2H-benzotriazole

When in Example 1, the 2-nitro-2'-hydroxy-3',5'-di-tert-amylazobenzene was replaced by an equivalent amount of 2-nitro-5-chloro-2'-hydroxy-3',5'-di-tert-butylazobenzene, the above noted product was obtained in a yield of 68.2%.

The use of this nickel catalyst did not result in any cleavage of the chlorine moiety from the molecule and none of the corresponding deschloro compound was observed.

EXAMPLE 9

5-Chloro-2-(2-hydroxy-3-tert-butyl-5-methylphenyl)-2H-benzotriazole

When in Example 1, the 2-nitro-2'-hydroxy-3',5'-di-tert-amylazobenzene is replaced by an equivalent amount of 2-nitro-5-chloro-2'-hydroxy-3'-tert-butyl-5-methylazobenzene, the above noted product is obtained.

EXAMPLE 10

2-(2-Hydroxy-3,5-di-tert-amylphenyl)-2H-benzotriazole

When using the general procedure of Example 1, 0.5% by weight of the wetting agent sorbitan monooleate, Span 80, was added to the hydrogenation system, the above named product was obtained in a 75.2% yield.

EXAMPLE 11

2-(2-Hydroxy-3,5-di-tert-amylphenyl)-2H-benzotriazole

When using the general procedure of Example 1, the molybdenum-promoted Raney nickel catalyst was replaced by an equivalent amount of unpromoted Raney nickel and with all other variables kept constant, the above named product was obtained in yields that were essentially the same as those obtained under the same conditions using the molybdenum-promoted Raney nickel catalyst.

These data are summarized in the table below:

| Run | 2% Raney Nickel Catalyst Added in 1 Portion | Hydrogenation Temperature °C. | Total Product Yield % |
|---|---|---|---|
| 1 | Not promoted | 48 | 64.6 |
| 2 | Not promoted | 38 | 56.2 |
| 3 | Molybdenum-promoted | 35–48 | 60.1 |
| 4 | Molybdenum-promoted | 35–38 | 56.1 |

EXAMPLE 12

2-(2-Hydroxy-5-methylphenyl)-2H-benzotriazole

When using the procedure of Example 1, the 2-nitro-2'-hydroxy-3',5'-di-tert-amylazobenzene was replaced by an equivalent amount of 2-nitro-2'-hydroxy-5'-methylazobenzene and a total of 9% molybdenum-promoted Raney nickel catalyst was used, the above named compound was obtained in a 60.3% yield.

EXAMPLE 13

2-(2-Hydroxy-5-methylphenyl)-2H-benzotriazole

When using the procedure of Example 4, the 6.0 grams of 50% slurry in water of molybdenum-promoted Raney nickel catalyst was replaced by 6.0 grams of a 50% slurry in water of a chromium-promoted Raney nickel catalyst and with all the chromium-promoted catalyst being added in one portion at the start of the hydrogenation, the above named product was isolated in yield of 72%.

EXAMPLE 14

2-(2-Hydroxy-3,5-di-tert-butylphenyl)-2H-benzotriazole

When using the procedure of Example 4, the 2-nitro-2'-hydroxy-5'-methylazobenzene was replaced by an equivalent amount of 2-nitro-2'-hydroxy-3,5-di-tert-butylazobenzene and using a total of 4 grams of molybdenum-promoted Raney nickel catalyst, the above named product was obtained in a yield of 49.2%.

EXAMPLE 15

2-(2-Hydroxy-5-methylphenyl)-2H-benzotriazole

When using the general procedure of Examples 4 or 5, the molybdenum-promoted Raney nickel catalyst was replaced by unpromoted Raney nickel catalyst and with other variables kept essentially constant, the above named product was obtained in yields that were essentially the same as with molybdenum-promoted Raney nickel catalyst.

These data are summarized in the table below:

| Run | Raney Nickel Catalyst * | Method of Example | Hydrogenation Temperature °C. | Total Product Yield % |
|---|---|---|---|---|
| 1 | Molybdenum-promoted | 5 | 45–60 | 72.0 |
| 2 | Not promoted | 5 | 45–60 | 60.9 |
| 3 | Not promoted | 4 | 55 | 70 |

Run 1, 4% catalyst in 2 portions;
Run 2, 9% catalyst in 3 portions;
Run 3, 4% catalyst in 1 portion.

EXAMPLE 16

2-(2-Hydroxy-3,5-di-tert-amylphenyl)-2H-benzotriazole

When using the general procedure of Example 5, the 2-nitro-2'-hydroxy-5'-methylazobenzene was replaced by an equivalent amount of 2-nitro-2'-hydroxy-3',5'-di-tert-amylazobenzene and the sodium hydroxide was replaced by an equivalent amount of potassium hydroxide, the hydrogenation was run in an Amsco mineral spirits/water (40/60) medium containing 1% sorbitan monooleate, Span 80, wetting agent at a hydrogen pressure of 6 atmospheres for a total period of 8 hours. The above named product was obtained in an isolated yield of 71.9%.

EXAMPLE 17

2-(2-Hydroxy-3,5-di-tert-butylphenyl)-2H-benzotriazole

When using the general procedure of Example 1, a 22% by weight suspension of 2-nitro-2'-hydroxy-3',5'-di-tert-butylazobenzene in isopropanol/triethylamine (1/0.18) was hydrogenated at 45° C. in the presence of a Raney nickel catalyst (6% by weight based on the azobenzene intermediate) for a period of 13 hours, the above named compound was obtained in a 67% yield.

When the amount of catalyst above was increased to 20% by weight based on the azobenzene, the hydrogenation was completed in 1.1 hour at 45° C. to give a 75% yield of product.

EXAMPLE 18

2-(2-Hydroxy-3,5-di-tert-butylphenyl)-2H-benzotriazole

Using the general procedure 6, 35.5 grams of 2-nitro-2'-hydroxy-3',5'-di-tert-butylazobenzene was suspended in 100 grams of tributyl phosphate, 50 grams of methanol and 4 grams of sodium hydroxide. To the suspension was then added 8 grams of Raney nickel catalyst and hydrogenation was carried out under 1 atmosphere of hydrogen at 45° C. for 7 hours. The catalyst was separated by filtration at 80° C. The above named product was obtained in the usual manner in a yield of 85.8%.

EXAMPLE 19

2-(2-Hydroxy-3,5-di-tert-amylphenyl)-2H-benzotriazole

When in Example 6, the 2-nitro-2'-hydroxy-5'-methylazobenzene was replaced by an equivalent amount of 2-nitro-2'-hydroxy-3',5'-di-tert-amylazobenzene and a total of 4% catalyst was used, the above named product was prepared in very high yield.

EXAMPLE 20

2-(2-Hydroxy-3,5-di-tert-amylphenyl)-2H-benzotriazole

When using the procedure of Example 1 the isopropanol and diethylamine were replaced by sufficient n-propylamine to give a 29% by weight solution of the 2-nitro-2'-hydroxy-3',5'-di-tert-amylazobenzene intermediate in the amine solvent, the hydrogenation was carried out at 45° C. and 50 psig (3.5 kg/cm$^2$) pressure. The excess amine solvent was removed by distillation and the above named product was obtained in a yield of 43.3%.

When the n-propylamine solvent above was replaced by a like weight of diethylamine and the hydrogenation was carried out at 15 psia (1 atmosphere), the yield of the above was 40.8%.

EXAMPLE 21

2-(2-Hydroxy-5-methylphenyl)-2H-benzotriazole

When using the procedure of Example 4 the toluene, methanol and diethylamine were replaced by sufficient n-propylamine to give a 29% by weight solution of 2-nitro-2'-hydroxy-5'-methylazobenzene intermediate, the above named product was isolated by removing most of the amine solvent by vacuum distillation and slurring the residue in methanol. The crude product was obtained in a yield of 88.4%.

A comparison of the effect of using various organic amines as solvent and base for the preparation of 2-(2-hydroxy-5-methylbenzyl)-2H-benzotriazole using the above procedure is shown in the table below:

| Amine Solvent | Reaction Time Minutes | Yield of Crude Product (%) |
|---|---|---|
| diethylamine | 210 | 59.0 |
| n-propylamine | 190 | 88.4 |
| dibutylamine | 150 | 74.0 |
| isopropylamine | 170 | 84.0 |
| tert-butylamine | 180 | 79.0 |
| triethylamine | 165 | 35.5 |
| n-butylamine | 130 | 79.0 |
| amylamine | 200 | 82.0 |
| morpholine | 240 | 72.0 |
| n-propylamine* with 20% water | 250 | 59.0 |
| n-propylamine* with 15% water | 220 | 74.0 |

*The presence of significant quantities of water in the organic amine solvent reduces the yield of the benzotriazole product.

What is claimed is:
1. A process for the production of 2-aryl-2H-benzotriazoles of the formula I

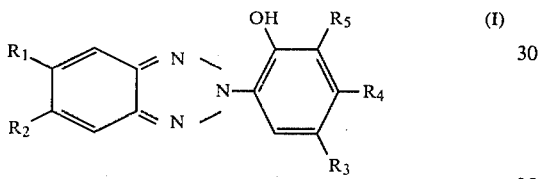

wherein
R$_1$ is hydrogen or chlorine, R$_2$ is hydrogen, chlorine, lower alkyl of 1 to 4 carbon atoms, lower alkoxy of 1 to 4 carbon atoms, carboalkoxy of 2 to 9 carbon atoms, carboxy or —SO$_3$H,
R$_3$ is alkyl of 1 to 12 carbon atoms, alkoxy of 1 to 4 carbon atoms, phenyl, phenyl substituted with alkyl groups, said alkyl groups having 1 to 8 carbon atoms, cycloalkyl of 5 to 6 carbon atoms, carboalkoxy of 2 to 9 carbon atoms, chlorine, carboxyethyl or phenylalkyl of 7 to 9 carbon atoms,
R$_4$ is hydrogen, lower alkyl of 1 to 4 carbon atoms, lower alkoxy of 1 to 4 carbon atoms, chlorine or hydroxyl, and
R$_5$ is hydrogen, alkyl of 1 to 12 carbon atoms, chlorine, cycloalkyl of 5 to 6 carbon atoms or phenylalkyl of 7 to 9 carbon atoms,
which comprises
reducing and cyclizing the corresponding o-nitroazobenzene

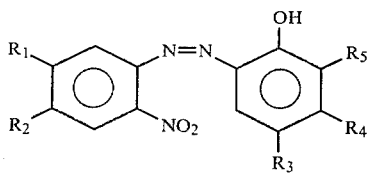

with hydrogen at a temperature in the range of from about 20° C. to about 100° C. and at a pressure in the range from about 15 psia (1.05 kg/cm$_2$, 1 atmosphere) to about 1000 psia (70 kg/cm$_2$, 66 atmospheres) while mixed in an alkaline medium, said medium consisting essentially of an organic solvent containing a water-soluble amine and having a pH greater than 10 in the presence of a nickel hydrogenation catalyst,
separating the catalyst which is suitable for recycle, and
recovering the desired 2-aryl-2H-benzotriazole.

2. A process according to claim 1 wherein said catalyst is a promoted nickel hydrogenation catalyst.

3. A process according to claim 2 wherein said hydrogenation catalyst is molybdenum-promoted Raney nickel or chromium-promoted Raney nickel.

4. A process according to claim 3 wherein said hydrogenation catalyst is molybdenum-promoted Raney nickel.

5. A process according to claim 1 which further comprises,
carrying out the reduction and cyclization in an solvent system containing an organic amine,
removing the nickel catalyst by filtration, and
recovering the desired 2-aryl-2H-benzotriazole.

6. A process according to claim 1 which further comprises,
carrying out the reduction and cyclization in an organic solvent system consisting essentially of an aliphatic or alicyclic amine or morpholine,
removing the nickel catalyst by filtration, and
recovering the desired 2-aryl-2H-benzotriazole.

7. A process according to claim 1 wherein said alkaline medium is a solution of a aromatic hydrocarbon, methanol and an aliphatic or alicyclic amine or morpholine.

8. A process according to claim 1 wherein said alkaline medium is a solution of an alkanol and an aliphatic or alicyclic amine or morpholine.

9. A process according to claim 1 wherein said alkaline medium is an aliphatic or alicyclic amine or morpholine.

10. A process according to claim 1 for the production of a compound of formula I wherein
R$_1$ is hydrogen,
R$_2$ is hydrogen, chlorine, lower alkyl of 1 to 2 carbon atoms, methoxy or carboxy,
R$_3$ is alkyl of 1 to 12 carbon atoms, cyclohexyl, phenyl, chlorine, α-methylbenzyl or carboxyethyl,
R$_4$ is hydrogen, hydroxyl or methyl, and
R$_5$ is alkyl of 1 to 12 carbon atoms, chlorine, cyclohexyl, benzyl or α-methylbenzyl.

11. A process according to claim 1 for production of a compound of formula I wherein
R$_1$ is hydrogen,
R$_2$ is hydrogen or chlorine,
R$_3$ is methyl, sec-butyl, tert-butyl, tert-amyl, tert-octyl, cyclohexyl, chlorine or carboxyethyl,
R$_4$ is hydrogen, and
R$_5$ is hydrogen, chlorine, methyl, tert-butyl, sec-butyl, tert-amyl, tert-octyl or α-methylbenzyl.

12. A process according to claim 1 for the production of 2-(2-hydroxy-5-methylphenyl)-2H-benzotriazole.

13. A process according to claim 1 for the production of 2-(2-hydroxy-5-tert-octylphenyl)-2H-benzotriazole.

14. A process according to claim 1 for the production of 2-(2-hydroxy-3,5-di-tert-amylphenyl)-2H-benzotriazole.

15. A process according to claim 1 for the production of 5-chloro-2-(2-hydroxy-3,5-di-tert-butylphenyl)-2H-benzotriazole.

16. A process according to claim 1 for the production of 5-chloro-2-(2-hydroxy-3-tert-butyl-5-methylphenyl)-2H-benzotriazole.

17. A process according to claim 1 for the production of 2-(2-hydroxy-3,5-di-tert butylphenyl)-2H-benzotriazole.

18. A process according to claim 1 wherein the amine is selected from the group consisting of primary aliphatic amines with alkyl groups of 1 to 6 carbon atoms, secondary aliphatic amines with alkyl groups of 1 to 6 carbon atoms, tertiary aliphatic amines with alkyl groups of 1 to 6 carbon atoms, piperidine, piperazine, morpholine, pyrrolidine and guanidine.

19. An improved process for the production of 2-aryl-2H-benzotriazoles of the formula I

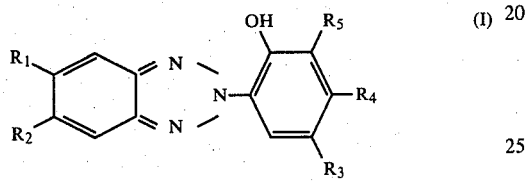

wherein
$R_1$ is hydrogen or chlorine,
$R_2$ is hydrogen, chlorine, lower alkyl of 1 to 4 carbon atoms, lower alkoxy of 1 to 4 carbon atoms, carboalkoxy of 2 to 9 carbon atoms, carboxy or —$SO_3H$,
$R_3$ is alkyl of 1 to 12 carbon atoms, alkoxy of 1 to 4 carbon atoms, phenyl, phenyl substituted with alkyl groups, said alkyl groups having 1 to 8 carbon atoms, cycloalkyl of 5 to 6 carbon atoms, carboalkoxy of 2 to 9 carbon atoms, chlorine, carboxyethyl or phenylalkyl of 7 to 9 carbon atoms,
$R_4$ is hydrogen, lower alkyl of 1 to 4 carbon atoms, lower alkoxy of 1 to 4 carbon atoms, chlorine or hydroxyl, and
$R_5$ is hydrogen, alkyl of 1 to 12 carbon atoms, chlorine, cycloalkyl of 5 to 6 carbon atoms or phenylalkyl of 7 to 9 carbon atoms,
by reducing and cyclizing the corresponding o-nitroazobenzene

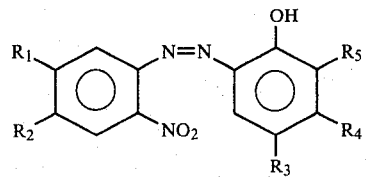

with hydrogen at a temperature in the range of from 20° C. to about 100° C. and at a pressure in the range from about 15 psia (1.05 kg.$cm_2$ 1 atmosphere) to about 1000 psia (70 kg/$cm_2$, 66 atmospheres) while mixed in an alkaline medium having a pH greater than 10 in the presence of a nickel hydrogenation catalyst and recovering the desired 2-aryl-2H-benzotriazole wherein the improvement comprises
using as the alkaline medium an aqueous alkaline or an aqueous hydrocarbon alkaline medium, said medium containing an alkali metal hydroxide and containing from 0.1 to 5% by weight of a dispersing agent which is a polyhydroxyalkyl monoester of a fatty acid.

20. An improved process according to claim 19 for the preparation of 2-(2-hydroxy-5-methylphenyl)-2H-benzotriazole.

21. An improved process according to claim 19 for the preparation of 2-(2-hydroxy-3,5-di-tert-amylphenyl)-2H-benzotriazole.

22. A process according to claim 19 wherein the dispersing agent is sorbitan monooleate.

23. A process according to claim 19 wherein said alkaline medium is an aqueous alkali metal hydroxide solution containing a water immiscible hydrocarbon and a dispersing agent.

UNITED STATES PATENT AND TRADEMARK OFFICE
CERTIFICATE OF CORRECTION

PATENT NO. : 4,219,480
DATED : August 26, 1980
INVENTOR(S) : Howard L. White and Casimir V. Krolewski It is certified that error appears in the above-identified patent and that said Letters Patent are hereby corrected as shown below:

Claim 5, column 28, lines 20 and 21 reads

"carrying out the reduction and cyclization in an solvent system containing an organic amine,"

should read

--carrying out the reduction and cyclization in an organic solvent system containing an amine,--.

Signed and Sealed this

Seventeenth Day of February 1981

[SEAL]

Attest:

RENE D. TEGTMEYER

Attesting Officer

Acting Commissioner of Patents and Trademarks